US011564846B2

(12) United States Patent
Askem

(10) Patent No.: US 11,564,846 B2
(45) Date of Patent: Jan. 31, 2023

(54) SYSTEMS AND METHODS FOR CONTROLLING OPERATION OF A REDUCED PRESSURE THERAPY SYSTEM TO DETECT LEAKS

(71) Applicant: Smith & Nephew PLC, Watford (GB)

(72) Inventor: Ben Alan Askem, Leeds (GB)

(73) Assignee: Smith & Nephew PLC, Watford (GB)

(*) Notice: Subject to any disclaimer, the term of this patent is extended or adjusted under 35 U.S.C. 154(b) by 0 days.

(21) Appl. No.: 17/505,356

(22) Filed: Oct. 19, 2021

(65) Prior Publication Data

US 2022/0031933 A1 Feb. 3, 2022

Related U.S. Application Data

(62) Division of application No. 16/328,547, filed as application No. PCT/EP2017/071693 on Aug. 30, 2017, now Pat. No. 11,167,075.

(Continued)

(51) Int. Cl.
*A61F 13/00* (2006.01)
*A61M 1/00* (2006.01)

(52) U.S. Cl.
CPC ......... *A61F 13/00068* (2013.01); *A61M 1/74* (2021.05); *A61M 1/96* (2021.05);
(Continued)

(58) Field of Classification Search
CPC .... A61F 13/00068; A61F 2013/00536; A61M 2205/15; A61M 2205/3331;
(Continued)

(56) References Cited

U.S. PATENT DOCUMENTS 7,678,090 B2 3/2010 Risk, Jr. et al.
7,763,000 B2 7/2010 Risk, Jr. et al.
(Continued)

FOREIGN PATENT DOCUMENTS

EP 2618860 B1 6/2015
JP 2014210020 A 11/2014
(Continued)

OTHER PUBLICATIONS

International Preliminary Reporton Patentability for Application No. PCT/EP2017/071693, dated Mar. 14, 2019, 8 pages.
(Continued)

*Primary Examiner* — Tatyana Zalukaeva
*Assistant Examiner* — Nhu Q. Tran
(74) *Attorney, Agent, or Firm* — Knobbe, Martens, Olson & Bear, LLP

(57) ABSTRACT

In some embodiments, a negative pressure apparatus includes a negative pressure source configured to provide negative pressure via a fluid flow path to a wound dressing placed to create a seal over a wound, a pressure sensor, and a controller. The controller can be configured to operate the negative pressure source in a first mode and determine a change in pressure in the fluid flow path over a period of time based on a plurality of measurements by the pressure sensor. In response to a determination that pressure in the fluid flow path is decreasing, the controller can operate the negative pressure source in a second mode in which greater amount of negative pressure is provided than in the first mode. In response to a determination that pressure in the fluid flow path is not decreasing, the controller can provide an indication of a first leak in the seal.

20 Claims, 4 Drawing Sheets

Related U.S. Application Data

(60) Provisional application No. 62/382,126, filed on Aug. 31, 2016.

(52) U.S. Cl.
CPC .... *A61F 2013/00536* (2013.01); *A61M 1/962* (2021.05); *A61M 1/985* (2021.05); *A61M 2205/15* (2013.01); *A61M 2205/3331* (2013.01); *A61M 2205/3344* (2013.01); *A61M 2205/50* (2013.01); *A61M 2205/583* (2013.01); *A61M 2205/70* (2013.01); *A61M 2205/702* (2013.01); *A61M 2205/8206* (2013.01)

(58) Field of Classification Search
CPC ...... A61M 2205/3344; A61M 2205/50; A61M 2205/583; A61M 2205/702; A61M 2205/8206
See application file for complete search history.

(56) References Cited

U.S. PATENT DOCUMENTS

| | | |
|---|---|---|
| 7,811,269 B2 | 10/2010 | Boynton et al. |
| 8,105,295 B2 | 1/2012 | Blott et al. |
| 8,167,869 B2 | 5/2012 | Wudyka |
| 8,235,972 B2 | 8/2012 | Adahan |
| 8,294,586 B2 | 10/2012 | Pidgeon et al. |
| 8,366,692 B2 | 2/2013 | Weston et al. |
| 8,377,016 B2 | 2/2013 | Argenta et al. |
| 8,444,392 B2 | 5/2013 | Turner et al. |
| 8,494,349 B2 | 7/2013 | Gordon |
| 8,663,200 B2 | 3/2014 | Weston et al. |
| 8,734,425 B2 | 5/2014 | Nicolini |
| 8,785,059 B2 | 7/2014 | Hartwell |
| 8,801,685 B2 | 8/2014 | Armstrong et al. |
| 8,814,841 B2 | 8/2014 | Hartwell |
| 8,834,451 B2 | 9/2014 | Blott et al. |
| 8,843,327 B2 | 9/2014 | Vernon-Harcourt et al. |
| 8,845,603 B2 | 9/2014 | Middleton et al. |
| 8,852,149 B2 | 10/2014 | Weston et al. |
| 8,852,170 B2 | 10/2014 | Weston et al. |
| 8,905,985 B2 | 12/2014 | Allen et al. |
| 8,945,074 B2 | 2/2015 | Buan et al. |
| 8,951,235 B2 | 2/2015 | Allen et al. |
| 8,974,429 B2 | 3/2015 | Gordon et al. |
| 9,067,003 B2 | 6/2015 | Buan et al. |
| 9,084,845 B2 | 7/2015 | Adie et al. |
| 9,220,823 B2 | 12/2015 | Nicolini |
| 9,227,000 B2 | 1/2016 | Fink et al. |
| 9,408,954 B2 | 8/2016 | Gordon et al. |
| 9,427,505 B2 | 8/2016 | Askem et al. |
| 9,526,817 B2 | 12/2016 | Blott et al. |
| 9,642,950 B2 | 5/2017 | Hartwell |
| 9,901,664 B2 | 2/2018 | Askem |
| 10,058,644 B2 | 8/2018 | Nicolini |
| 10,105,473 B2 | 10/2018 | Nicolini |
| 10,143,783 B2 | 12/2018 | Adie et al. |
| 10,155,070 B2 | 12/2018 | Childress et al. |
| 10,328,188 B2 | 6/2019 | Deutsch et al. |
| 10,799,623 B2 | 10/2020 | Lawhorn |
| 2006/0129137 A1 | 6/2006 | Lockwood et al. |
| 2007/0118096 A1 | 5/2007 | Smith et al. |
| 2007/0185463 A1 | 8/2007 | Mulligan |
| 2009/0299306 A1 | 12/2009 | Buan |
| 2011/0015593 A1 | 1/2011 | Svedman et al. |
| 2011/0077605 A1 | 3/2011 | Karpowicz et al. |
| 2012/0001762 A1 | 1/2012 | Turner et al. |
| 2012/0271256 A1 | 10/2012 | Locke et al. |
| 2013/0110058 A1 | 5/2013 | Adie et al. |
| 2014/0115893 A1 | 5/2014 | Pratt et al. |
| 2015/0133829 A1 | 5/2015 | DeBusk et al. |
| 2015/0217032 A1 | 8/2015 | Allen et al. |
| 2017/0216501 A1 | 8/2017 | Armstrong et al. |
| 2019/0022288 A1 | 1/2019 | Nicolini |
| 2019/0167863 A1 | 6/2019 | Adie et al. |

FOREIGN PATENT DOCUMENTS

| | | |
|---|---|---|
| WO | WO-2006052745 A2 | 5/2006 |
| WO | WO-2013064852 A1 | 5/2013 |
| WO | WO-2015023515 A1 | 2/2015 |
| WO | WO-2016018448 A1 | 2/2016 |
| WO | WO-2016109041 A1 | 7/2016 |
| WO | WO-2018041854 A1 | 3/2018 |
| WO | WO-2018164803 A1 | 9/2018 |

OTHER PUBLICATIONS

International Search Report and Written Opinion for Application No. PCT/EP2017/071693, dated Nov. 16, 2017, 11 pages.

SYSTEMS AND METHODS FOR CONTROLLING OPERATION OF A REDUCED PRESSURE THERAPY SYSTEM TO DETECT LEAKS

CROSS-REFERENCE TO RELATED APPLICATIONS

This application is a divisional of U.S. patent application Ser. No. 16/328,547, filed on Feb. 26, 2019, which is a US national phase of International Application No, PCT/EP2017/071693, filed on Aug. 30, 2017, which claims priority to U.S. Provisional Patent Application No. 62/382,126, filed on Aug. 31, 2016, each of which is incorporated by reference it its entirety and is made part of this disclosure.

BACKGROUND

Field

Embodiments of the present disclosure relate to methods and apparatuses for dressing and treating a wound with topical negative pressure (TNP) therapy. In particular, but without limitation, embodiments disclosed herein relate to negative pressure therapy pumps and dressings, and methods and systems for controlling the operation of TNP systems.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates and may reduce bacterial load and thus, infection to the wound. Furthermore, TNP therapy permits less outside disturbance of the wound and promotes more rapid healing.

SUMMARY

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

In some embodiments, a negative pressure wound therapy apparatus includes a negative pressure source configured to provide negative pressure via a fluid flow path to a dressing placed over a wound to create a seal over the wound, a pressure sensor configured to measure pressure in the fluid flow path, and a controller. A controller can be configured to, in response to a request to initiate or restart application of negative pressure, operate the negative pressure source in a first mode and determine a change in pressure in the fluid flow path over a period of time based on a plurality of measurements by the pressure sensor over the period of time. The controller can also be configured to, in response to a determination that pressure in the fluid flow path is decreasing, operate the negative pressure source in a second mode in which the negative pressure source provides a greater amount of negative pressure than in the first mode. The controller can also be configured to, in response to a determination that pressure in the fluid flow path is not decreasing, provide an indication of a first leak in the seal.

The apparatus of the preceding paragraph can include one or more of the following features. The request to initiate or restart application of negative pressure can be associated with a negative pressure set point to be established in the fluid flow path. Operation of the negative pressure source in the first mode can be insufficient to reduce pressure in the fluid flow path to establish the negative pressure set point. Operation of the negative pressure source in the second mode can be sufficient to reduce pressure in fluid flow path to establish the negative pressure set point.

The apparatus of any of the preceding paragraphs can include one or more of the following features. Operation of the negative pressure in the second mode can include the controller being further configured to activate the negative pressure source to reduce pressure in the fluid flow path to the negative pressure set point; if pressure in the fluid flow path has not reached the negative pressure set point over a first period of time, deactivate the negative pressure source for a second period of time; and in response to a determination that the second period of time has elapsed, activate the negative pressure source to reduce pressure in the fluid flow path to establish the negative pressure set point.

The apparatus of any of the preceding paragraphs can include one or more of the following features. The controller can be further configured to monitor a number of deactivations of the negative pressure source for the second period of time. The controller can be further configured to provide an indication of a second leak in the seal in response to a determination that the number of the negative pressure source exceeds a retry threshold. The first leak can be a leak of smaller intensity than the second leak. Indication of at least one of the first or second leaks in the seal can include deactivation of the source of negative pressure. Operation of the negative pressure source in the first mode can include establishment of a flow rate of about 25 mL/min in the fluid flow path. Indication of the first leak in the seal can correspond to an indication of a leak with flow of about 25 mL/min or less.

The apparatus of any of the preceding paragraphs can include one or more of the following features. The controller can be configured to determine the change in pressure in the fluid flow path based on a determination of a difference in a first pressure in the fluid flow path measured by the pressure sensor and a second pressure in the fluid flow path subsequently measured by the pressure sensor. The first mode can be a low flow mode. The controller can be configured to operate the negative pressure source in the first mode based on a first drive signal provided to an actuator of the negative pressure source. The controller can be configured to operate the negative pressure source in the second mode based on a second drive signal provided to the actuator of the negative pressure source, the second drive signal being different from the first drive signal.

In some embodiments, a method of operating a negative pressure wound therapy apparatus includes, by a controller, in response to a request to initiate or restart application of negative pressure, operating a negative pressure source in a first mode. The negative pressure source can be configured to provide negative pressure via a fluid flow path to a dressing placed over a wound to create a seal over the wound. The method can also include determining a change in pressure in the fluid flow path over a period of time based on a plurality of measurements by a pressure sensor over the period of time. The method can also include, in response to determining that pressure in the fluid flow path is decreasing, operating the negative pressure source in a second mode in which the negative pressure source provides a greater amount of negative pressure than in the first mode. The method can also include, in response to determining that pressure in the fluid flow path is not decreasing, providing an indication of a first leak in the seal.

The method of the preceding paragraph can include one or more of the following features. The request to initiate or restart application of negative pressure can be associated with a negative pressure set point to be established in the fluid flow path. Operating the negative pressure source in the first mode can be insufficient to reduce pressure in the fluid flow path to establish the negative pressure set point. Operating the negative pressure source in the second mode can be sufficient to reduce pressure in fluid flow path to establish the negative pressure set point.

The method of any of the preceding paragraphs can include one or more of the following features. Operating the negative pressure in the second mode further includes: activating the negative pressure source to reduce pressure in the fluid flow path to the negative pressure set point; if pressure in the fluid flow path has not reached the negative pressure set point over a first period of time, deactivating the negative pressure source for a second period of time; and in response to determining that the second period of time has elapsed, activating the negative pressure source to reduce pressure in the fluid flow path to establish the negative pressure set point.

The method of any of the preceding paragraphs can include one or more of the following features. The method can include monitoring a number of deactivations of the negative pressure source for the second period of time. The method can include providing an indication of a second leak in the seal in response to determining that the number of the negative pressure source exceeds a retry threshold. The first leak can be a leak of smaller intensity than the second leak. Indication of at least one of the first or second leaks in the seal can include deactivating the source of negative pressure. Operating the negative pressure source in the first mode can include establishing a flow rate of about 25 mL/min in the fluid flow path. Indication of the first leak in the seal can correspond to an indication of a leak with flow of about 25 mL/min or less.

The method of any of the preceding paragraphs can include one or more of the following features. Determining the change in pressure in the fluid flow path can be further based on determining a difference in a first pressure in the fluid flow path measured by the pressure sensor and a second pressure in the fluid flow path subsequently measured by the pressure sensor. The first mode can be a low flow mode. Operating the negative pressure source in the first mode can further include providing a first drive signal to an actuator of the negative pressure source. Operating the negative pressure source in the second mode can further include providing a second drive signal to the actuator of the negative pressure source, the second drive signal being different from the first drive signal.

BRIEF DESCRIPTION OF THE DRAWINGS

Embodiments of the present disclosure will now be described hereinafter, by way of example only, with reference to the accompanying drawings in which.

DETAILED DESCRIPTION OF EMBODIMENTS

Overview

Embodiments disclosed herein relate to apparatuses and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). In some embodiments, local ambient atmospheric pressure is used as a reference point, and such local atmospheric pressure may not necessarily be, for example, 760 mmHg. Accordingly, a negative pressure value of −X mmHg reflects absolute pressure that is X mmHg below, for example, 760 mmHg or, in other words, pressure of (760-X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg).

The negative pressure range for some embodiments of the present disclosure can be approximately −80 mmHg, or between about −20 mmHg and −200 mmHg or more. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

Embodiments of the present disclosure are generally applicable to use in topical negative pressure ("TNP") therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Reduced Pressure Therapy Systems and Methods

Figure 1:
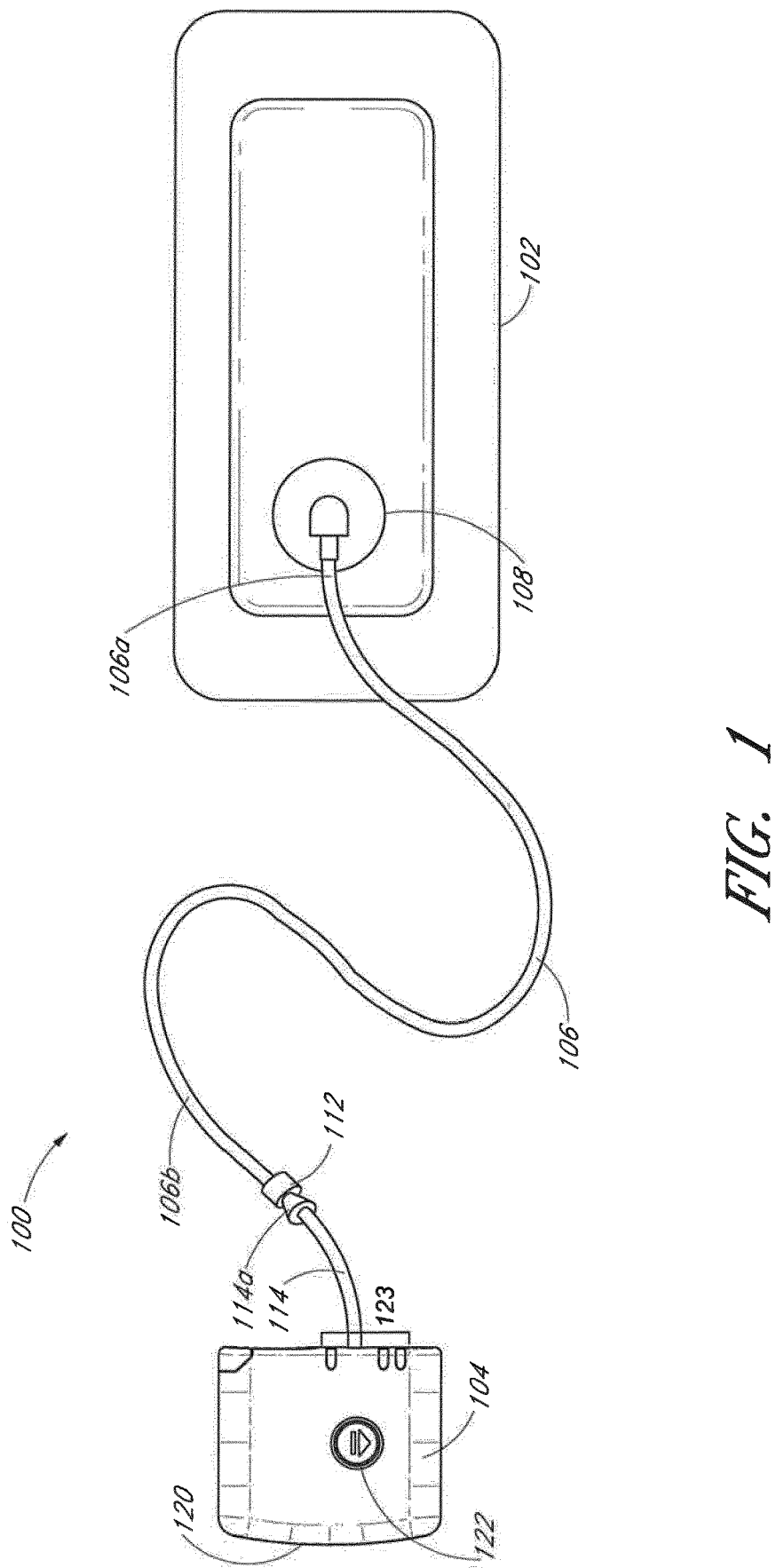
FIG. 1 illustrates an embodiment of a reduced pressure wound therapy apparatus including a pump, a dressing, and a conduit.

FIG. 1 illustrates an embodiment of a reduced pressure wound treatment apparatus 100 comprising a wound dressing 102 in combination with a negative pressure source 104, which is illustrated as a pump assembly. In any of the apparatus embodiments disclosed herein, as in the embodiment illustrated in FIG. 1, the negative pressure source can be a canisterless negative pressure source (meaning that the negative pressure source does not have an exudate or liquid collection canister). However, any of the embodiments disclosed herein can be configured to include or support a canister. Additionally, in any of the apparatus embodiments disclosed herein, any of the negative pressure source embodiments can be mounted to, embedded within, or supported by the dressing, or adjacent to the dressing. The dressing 102 may be placed over a wound (not illustrated), and a conduit 106 may then be connected to the dressing 102. Dressing 102 or any other dressing disclosed herein can be made of any suitable materials, sizes, components, etc. The conduit 106 or any other conduit disclosed herein can be formed from polyurethane, PVC, nylon, polyethylene, silicone, or any other suitable material.

Some embodiments of the dressing 102 can have a port 108 configured to receive an end of the conduit 106 (e.g., the first end 106a of the conduit 106), though such port 108 is not required. In some embodiments, the conduit can otherwise pass through and/or under the dressing 102 to supply a source of reduced pressure to a space between the dressing 102 and the wound so as to maintain a desired level of reduced pressure in such space. Some embodiments of the apparatus 100 can be configured such that the first end 106a of the conduit 106 is pre-attached to the port 108. The conduit 106 can be any suitable article configured to provide at least a substantially sealed fluid flow pathway between the negative pressure source 104 and the dressing 102, so as to supply the reduced pressure provided by the negative pressure source 104 to the dressing 102. In some embodiments, the port 108 can be made of soft, flexible materials such that, for example, the user would experience little or no discomfort if the user lies or otherwise puts pressure on the dressing 102 and/or the port 108.

The dressing 102 can be provided as a single article with all wound dressing elements (including the port 108) pre-attached and integrated into a single unit. The wound dressing 102 may then be connected, via the conduit 106, to a source of negative pressure such as the negative pressure source 104. In some embodiments, though not required, the negative pressure source 104 can be miniaturized and portable, such as the PICO™ pump, although larger conventional pumps, such as the EZ CARE™ pump, can also be used with the dressing 102. The pump can be a diaphragm pump (or any other type of negative pressure pump) actuated by an electric motor, a voice-coil actuator, a piezoelectric actuator, etc.

The wound dressing 102 can be located over a wound site to be treated. The dressing 102 can form a substantially sealed cavity or enclosure over the wound site. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

In some embodiments, it may be preferable for the wound site to be filled partially or completely with a wound packing material. This wound packing material is optional, but may be desirable in certain wounds, for example deeper wounds. The wound packing material can be used in addition to the wound dressing 102. The wound packing material generally can comprise a porous and conformable material, for example foam (including reticulated foams), and gauze. Preferably, the wound packing material is sized or shaped to fit within the wound site so as to fill any empty spaces. The wound dressing 102 can then be placed over the wound site and wound packing material overlying the wound site. When a wound packing material is used, once the wound dressing 102 is sealed over the wound site, TNP is transmitted from a pump through the wound dressing 102, through the wound packing material, and to the wound site. This negative pressure draws wound exudate and other fluids or secretions away from the wound site.

In some embodiments, the conduit 106 can have a connector 112 positioned at a second end 106b of the conduit 106. The connector 112 can be configured to couple with a short length of conduit 114 projecting from the negative pressure source 104, with a mating connector 114a in communication with the short length of conduit 114, with a connector supported by the pump housing, or otherwise. The length of the tubing 114 in some embodiments can be approximately 14 mm (0.55 in), or from approximately 0.5 in to approximately 5 inches. The short length of conduit or tubing 114 can decrease the discomfort to a patient while laying or otherwise resting on the pump and connector 112. Configuring the negative pressure source 104 and conduit 106 so that the conduit 106 can be quickly and easily removed from the negative pressure source 104 can facilitate or improve the process of dressing or pump changes, if necessary. Any of the pump embodiments disclosed herein can be configured to have any of the connection configurations disclosed herein between the tubing and the pump.

In some embodiments, as in the illustrated embodiment, the negative pressure source 104 can be of a sufficiently small and portable size to be supported on a user's body or in a user's clothing or on the dressing 102. For example, the negative pressure source 104 can be sized to be attached using adhesive medical tape or otherwise to a person's skin in a comfortable location, adjacent to or on the dressing 102 or otherwise. Further, the negative pressure source 104 can be sized to fit within a person's pants or shirt pocket, or can be tethered to a person's body using a lanyard, pouch, or other suitable device or article.

Some embodiments of the apparatus 100 are designed to operate without the use of an exudate canister. The dressing 102 can be configured to have a film having a high water vapour permeability to enable the evaporation of surplus fluid, and can have a superabsorbing material contained therein to safely absorb wound exudate. Some embodiments of the apparatus are designed for single-use therapy and can be disposed of in an environmentally friendly manner after an approximately maximum usage of from seven to eleven days. The pump can be programmed to automatically terminate therapy after a desired number of days, e.g., after seven days, further operation of the pump will not be possible. Some embodiments are designed for longer or repeated usage, and can be configured to support an exudate canister.

In some embodiments, the system 100 provides indication, alarms, etc. to the user reflecting operating conditions. The system 100 can include visual, audible, tactile, and other types of indicators and/or alarms configured to signal to the user various operating conditions. Such conditions include system on/off, standby, pause, normal operation, dressing problem, leak, error, and the like. The indicators and/or alarms can include one or more speakers, displays, light sources, etc., and/or combinations thereof. For example, indication can be provided by activating or deactivating the source of negative pressure, reducing negative pressure level generated by the source of negative, lowering the amount of power used by the source of negative pressure, etc. or any combination thereof.

As is illustrated in FIG. 1, indicators 123 can be one or more light emitting diodes (LEDs). The indicators 123 can be positioned on a housing 120 of the negative pressure source 104 and can be configured to alert a user to a variety of operating and/or failure conditions of the negative pressure source, including alerting the user to normal or proper operating conditions, pump failure, power supplied to the pump or power failure, the condition or voltage level of the batteries, detection of a leak within the dressing (e.g., in the seal) or flow pathway, suction blockage, or any other similar or suitable conditions or combinations thereof. In some embodiments, the indicators 123 can include a battery indicator, an OK indicator, and a dressing indicator. The negative pressure source 104 can also have a control button 122 (which can also be a switch or other similar component).

The fluidic connection between the dressing 102 and the negative pressure source 104 can be referred to as the fluid flow path.

In some embodiments, such as when the negative pressure source 104 is mounted to or embedded within the dressing 102, portions of or the entirety of one or more of the conduit 106, the port 108, the connector 112, or the short length of conduit 114 can be omitted.

In some embodiments, the negative pressure source 104 is controlled by at least one controller, which can be coupled to at least one memory.

Figure 2:
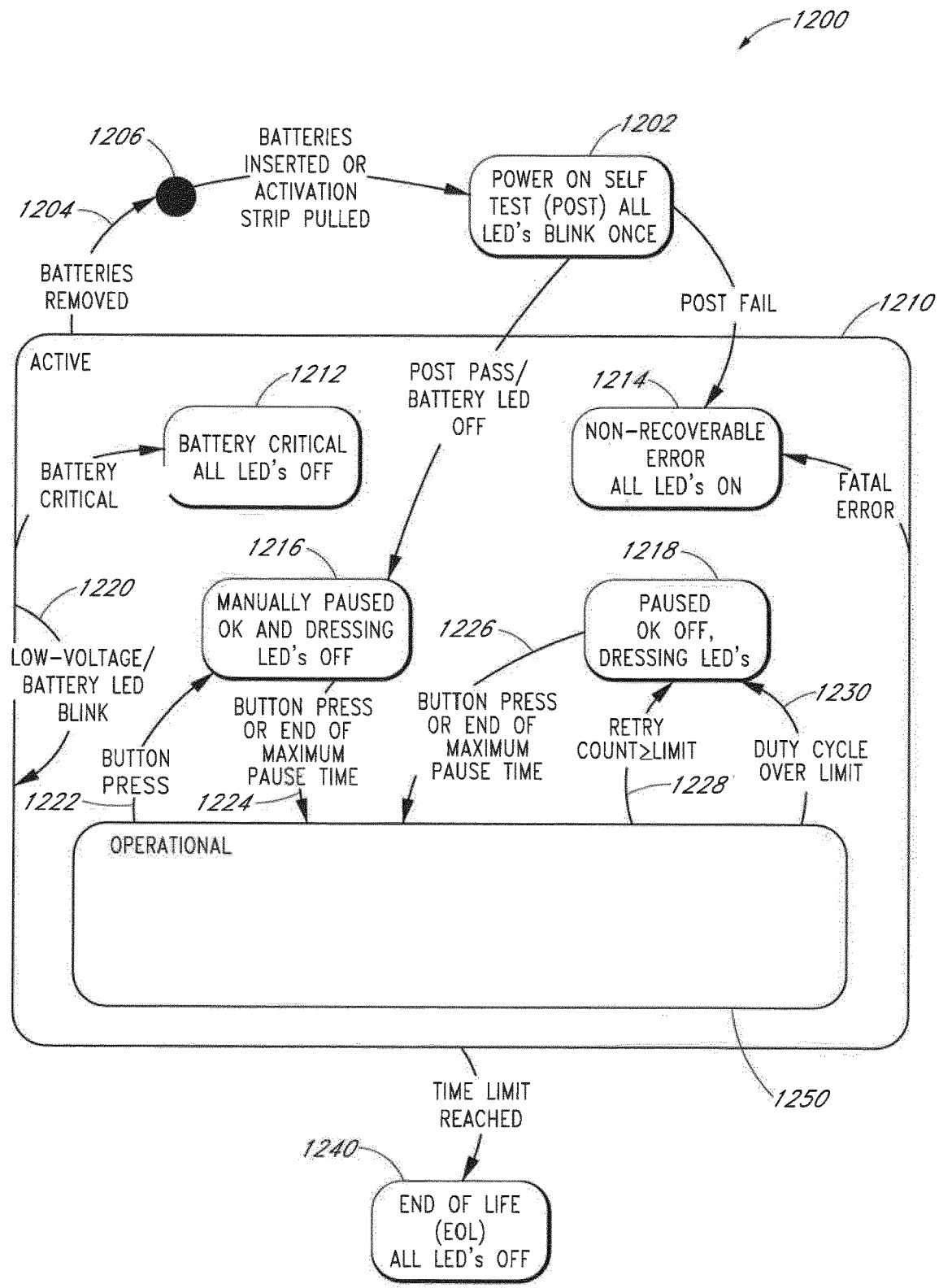
FIG. 2 illustrates a top level state diagram of operation of a negative pressure source according to some embodiments.
Figure 3:
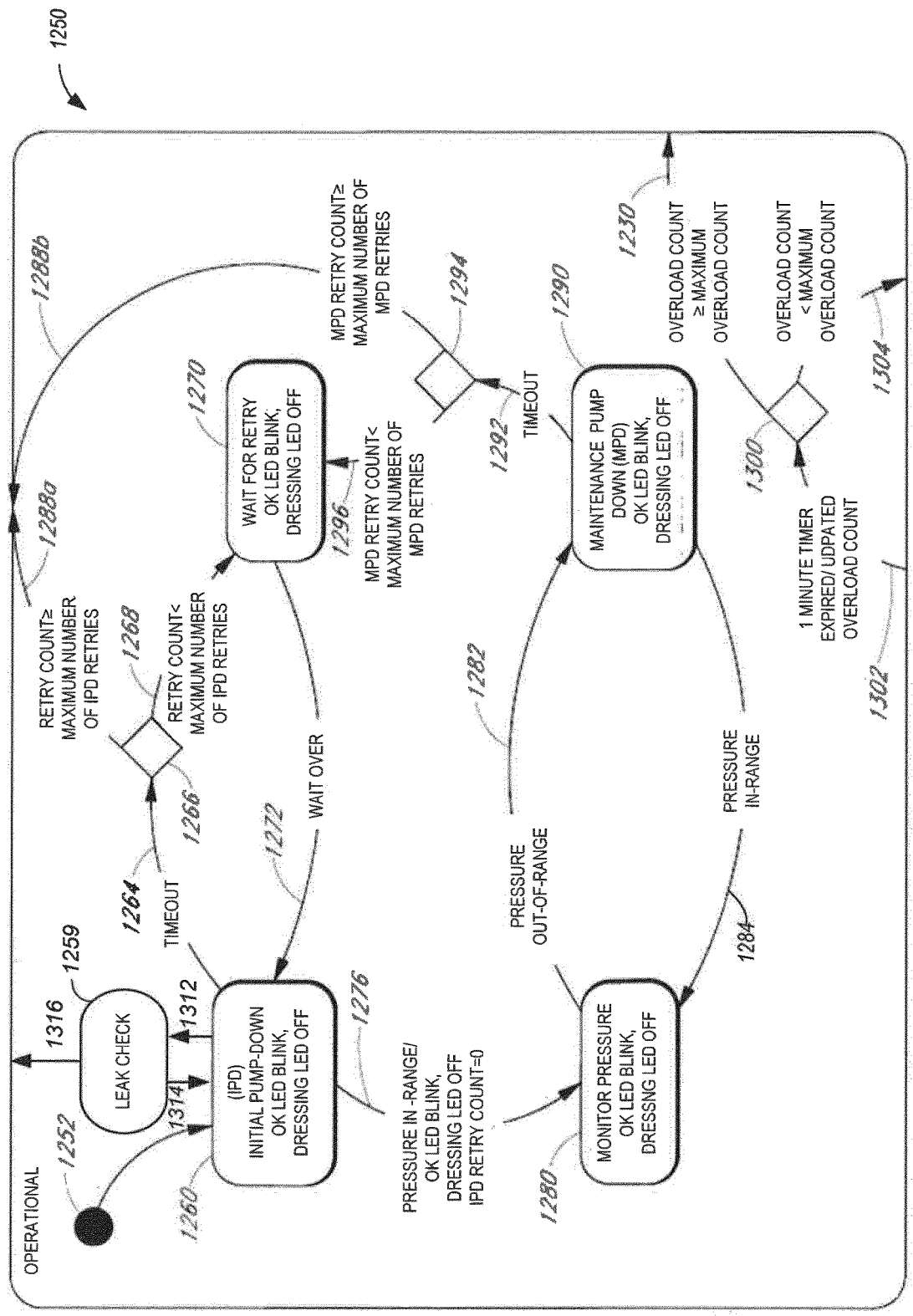
FIG. 3 illustrates an operational state diagram of operation of a negative pressure source according to some embodiments.

Systems and Methods for Controlling the Negative Pressure Source to Detect Leaks In some embodiments, the negative pressure source 104 can be configured to control the operation of system. For example, the negative pressure source 104 can be configured to provide a suitable balance between uninterrupted delivery of therapy and/or avoidance of inconveniencing the user by, for example, frequently or needlessly pausing or suspending therapy and a desire to conserve power, limit noise and vibration generated by the negative pressure source, etc. FIG. 2 illustrates a top level state diagram 1200 of operation of the negative pressure source according to some embodiments. In some embodiments, a controller of the negative pressure source can be configured to implement the flow of the state diagram 1200. As is illustrated in FIG. 2, the operation of the negative pressure source can, in some embodiments, be grouped into four general state categories: inactive/initialization (states 1206 and 1202), active 1210, operational 1250, and end of life (state 1240). As is illustrated in FIGS. 2 and 3, state categories 1210 and 1250 each comprises multiple states and transitions between states.

In some embodiments, so long as a power source (e.g., one or more batteries) is not connected to the negative pressure source or removed (as is illustrated by the transition 1204), or the negative pressure source has not been activated (e.g., by pulling an activation strip, triggering a switch, or the like), the negative pressure source remains in state 1206. While remaining in this state, the negative pressure source can remain inactive. When the power source is connected and/or the negative pressure source has been activated for a first time, the negative pressure source transitions to state 1202, where power on self-test(s) (POST) can be performed. Power on self-test(s) can include performing various checks to ensure proper functionality of the system, such as testing a memory (e.g., performing a check, such as a cyclic redundancy check, of the program code to determine its integrity, testing the random access memory, etc.), reading a pressure sensor to determine whether the pressure values are within suitable limits, reading the remaining capacity or life of the power source (e.g., battery voltage, current, etc.) to determine whether it is within suitable limits, testing the negative pressure source, and the like. As is illustrated, indicators (e.g., one or more LEDs, one or more LCDs, etc.) can be configured to indicate to the user (e.g., by blinking or flashing once) that the negative pressure source is undergoing POST test(s).

In some embodiments, if one or more of POST test(s) fail, the negative pressure source can transition to non-recoverable error state 1214. While in this state, the negative pressure source can deactivate therapy, and the indicators 123 can be configured and indicate to the user that an error was encountered. In some embodiments, all indicators can be configured to remain active. Based on the severity of error, in some embodiments, the negative pressure source can be configured to recover from the error and continue operation (or transition to the non-recoverable error state 1214). As is illustrated, the negative pressure source can transition to state 1214 upon encountering a fatal error during operation. Fatal errors can include program memory errors, program code errors (e.g., encountering an invalid variable value), controller operation errors (e.g., watchdog timer expires without being reset by the controller), component failure (e.g., inoperative negative pressure source, inoperative pressure sensor, etc.), and any combination thereof.

When POST test(s) pass, in some embodiments, the negative pressure source can transition to a manually paused state 1216. As is illustrated, this transition can be indicated to the user by deactivating one of indicators 123 (e.g., the battery indicator). When the negative pressure source transitions into and remains in the manually paused state 1216, the user can be provided an indication, such as by deactivating one or more indicators (e.g., the OK indicator and the dressing indicator). In some embodiments, therapy can be suspended while the negative pressure source remains in the manually paused state 1216. For example, the source of negative pressure (e.g., pump) can be deactivated (or turned off). In some embodiments, indication can be provided by deactivating the source of negative pressure.

In some embodiments, the negative pressure source can be configured to make a transition 1224 from the manually paused state 1216 to the operational state category 1250 (where the negative pressure source is configured to deliver therapy) in response to receiving a signal from the switch.

For example, the user can press a button to start, suspend, and/or restart therapy. In some embodiments, the negative pressure source can be configured to monitor the duration of time the negative pressure source remains in the manually paused state 1216. This can be accomplished, for example, by maintaining a timer (in firmware, software, hardware or any combination thereof), which can be reset and started when the negative pressure source transitions into the manually paused state 1216. The negative pressure source can be configured to automatically make the transition 1224 from the manually paused state 1216 to the operational state category 1250 when the time duration exceeds a threshold. In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the negative pressure source nears the end of life (as is explained below), the threshold can be decreased. In some embodiments, the user can pause therapy by activating the switch (e.g., pressing the button), thereby causing the negative pressure source to make a transition 1222 from the operational state category 1250 to the manually paused state 1216. In some embodiments, the negative pressure source can be configured so that the user can only pause therapy, whereas disconnecting the power source (e.g., removing batteries) stops therapy.

In some embodiments, the negative pressure source can be configured to include a paused state 1218. When the negative pressure source transitions into and remains in the paused state 1218, the user can be provided an indication. For example, the negative pressure source can be configured to deactivate the OK indicator and cause the dressing indicator to flash or blink. In some embodiments, therapy can be suspended while the negative pressure source remains in the manually paused state 1216. For example, the source of negative pressure (e.g., pump) can be deactivated (or turned off), which provides the indication to the user that the negative pressure source is in the paused state 1218. As is explained below, in some embodiments, the negative pressure source can be configured to transition from the operational state category 1250 into the paused state 1218 when a number of retry cycles exceeds a retry limit (transition 1228) or when duty cycle is determined to exceed a duty cycle limit (transition 1230). In some embodiments, transitions 1228 and 1230 can reflect the presence of a leak in the system.

In some embodiments, the negative pressure source can be configured to make a transition 1226 from the paused state 1218 to the operational state category 1250 (where the negative pressure source is configured to activate the pump to deliver therapy) in response to receiving a signal from the switch (e.g., the user pressing a button to restart therapy). In some embodiments, the negative pressure source can be configured to monitor the duration of time the negative pressure source remains in the paused state 1218. For example, this can be accomplished by maintaining a timer (in firmware, software, hardware or any combination thereof), which can be reset and started when the negative pressure source transitions into the paused state 1218. The negative pressure source can be configured to automatically make the transition 1226 from the paused state 1218 to the operational state category 1250 when the time duration exceeds a threshold. The threshold can be the same or different than the threshold of the manually paused state 1216 described herein. In some embodiments, the threshold can be a preset value, such as between 1 minute or less and 1 hour or more. In some embodiments, the threshold can be set or changed by the user. In some embodiments, the threshold can be varied based on various operating conditions or on any combination thereof. For example, as the negative pressure source nears the end of life (as is explained below), the threshold can be decreased.

In some embodiments, the negative pressure source includes both the manually paused state 1216 and the paused state 1218 in order to differentiate between various causes for pausing therapy. Such ability to differentiate can allow the negative pressure source to provide the user with an indication of a particular cause for pausing therapy (e.g., manually paused state 1216 and paused state 1218 can provide different indications). For example, therapy can be paused due to the user manually pressing the button, in which case the negative pressure source can make the transition 1222 from the operational state category 1250 to the manually paused state 1216. As another example, therapy can be paused due to detecting a leak, in which case the negative pressure source can make the transition 1228 and/or 1230 from the operational state category 1250 to the paused state 1218. In some embodiments, the negative pressure source can be configured to include one state indicating a suspension or pause in the delivery of therapy or more than two such states.

In some embodiments, the negative pressure source can be configured to monitor the remaining capacity or life of the power source (e.g., by periodically reading or sampling the battery voltage, current, etc.). The negative pressure source can be configured to indicate to the user the remaining capacity. For example, if the power source is determined to have a normal remaining capacity (e.g., as a result of comparison to a threshold, such as 2.7V, 2.6V, 2.5V, etc.), the battery indicator can be deactivated. If the power source is determined to have low remaining capacity, the negative pressure source can be configured to provide an indication to the user by, for example, causing the battery indicator to blink or flash, as is illustrated by the transition 1220. In some embodiments, the battery indicator can be configured to be blinking or flashing intermittently or continuously regardless of the state the negative pressure source is in or only in particular states.

In some embodiments, when the remaining capacity of the power source is determined to be at or near a critical level (e.g., as a result of comparison to a threshold, such as 2.4V, 2.3V, 2.2V, etc.), the negative pressure source can be configured to transition into a battery critical state 1212. In some embodiments, the negative pressure source can be configured to remain in this state until the capacity of the power source is increased, such as by replacing or recharging the power source. The negative pressure source can be configured to deactivate therapy while remaining in the battery critical state 1212. In addition, as is illustrated, the negative pressure source can be configured to indicate to the user that the power source is at or near the critical level by, for example, deactivating all indicators.

In some embodiments, the negative pressure source can be configured to provide therapy for a predetermined period of time, such as approximately 1 day, 2-10 days, etc. following a first activation. In some embodiments, such period of time can be a preset value, changed by the user, and/or varied based on various operating conditions or on any combination thereof. The negative pressure source can be disposed upon the expiration of such period of time. In some embodiments, the first activation can be reflected by a transition into the active state category 1210, by pulling the activation strip (e.g., transition into state 1202), etc. Once the negative pressure source has been activated, the negative pressure source can be configured to monitor the duration it has remained active. In some embodiments, the negative pressure source can be configured to monitor the cumulative duration of remaining in the active state category 1210. This can be accomplished, for example, by maintaining a timer (in firmware, software, hardware or any combination thereof), that reflects such duration.

When the duration reaches or exceeds a threshold (e.g., 7 days, 10 days, etc.), the negative pressure source can be configured to transition to an end of life (EOL) state 1240. The negative pressure source can be configured to deactivate therapy while remaining in state 1240 and to indicate to the user that end of negative pressure source' usable life has been reached. For example, the negative pressure source can be configured to deactivate all indicators and/or deactivate the button. In some embodiments, when the negative pressure source is disposable, transitioning to the end of life state 1240 means that the negative pressure source can be disposed of. The negative pressure source can be configured to disable reactivation of the negative pressure source once the end of life has been reached. For example, the negative pressure source can be configured to not allow reactivation even if the power source is disconnected and reconnected later, which can be accomplished by storing an indication, value, flag, etc. in the read only memory.

FIG. 3 illustrates the operational flow in state category 1250 of the negative pressure source 104 according to some embodiments. The negative pressure source can be configured to deliver therapy, monitor leaks in the system, provide indication(s) to the user, and the like. As is explained below, in some embodiments, the negative pressure source can be configured to deliver therapy by initially attempting to establish a first set point or desired negative pressure level (e.g., negative pressure between −5 mmHg or less and −200 mmHg or more, such as −100 mmHg) in the fluid flow path (e.g., under the dressing 102). In some embodiments, the first desired negative pressure level can be a preset value, set or changed by the user, and/or varied based on various operating conditions or on any combination thereof. Once the first desired negative pressure level is established in the fluid flow path, the negative pressure source can be configured to deactivate the source of negative pressure (e.g., pump). When negative pressure in the fluid flow path (e.g., under the dressing 102) decreases (e.g., gravitates toward standard atmospheric pressure) due to leaks in the system, the negative pressure source can be configured to restore negative pressure in the fluid flow path by activating the pump to establish a second set point or desired negative pressure level in the fluid flow path (e.g., negative pressure between −5 mmHg or less and −200 mmHg or more, such as −100 mmHg). In some embodiments, the second desired negative pressure level can be a preset value, set or changed by the user, and/or varied based on various operating conditions or on any combination thereof. In some embodiments, the first and second desired negative pressure levels can be the same. In some embodiments, the first and second desired negative pressure levels can be different, that is, the second negative pressure level can be less than the first negative pressure level or vice versa.

In some embodiments, the negative pressure source can transition from the manually paused state 1216 and/or paused state 1218 to state 1252. As is explained herein, this transition can be caused by the user pressing the button to start/restart therapy and/or upon expiration of duration of time, such as 1 hour. The negative pressure source can be configured to immediately transition to an initial pump down (IPD) state 1260, where the negative pressure source can be activated to establish the first desired negative pressure level in the fluid flow path. In some embodiments, the negative pressure source can be activated if the pressure level in the fluid flow path is above (less than) the first desired negative pressure level. Activating the source of negative pressure to establish the first desired negative pressure level in the fluid flow path (e.g., under the dressing 102) can be referred to herein as the "initial pump down." The negative pressure source can be configured to indicate to the user that it is performing the initial pump down by, for example, causing the OK indicator to blink or flash and deactivating the dressing indicator. In some embodiments, the indication can be provided by, for example, activating the source of negative pressure. The negative pressure source can be configured to measure the level of pressure in the fluid flow path by reading or sampling the sensor. The pressure sensor can be positioned in any suitable location in the fluid flow path, such as at or near the pump inlet, under or near the dressing, etc. In some embodiments, more than one pressure sensor is positioned in the fluid flow path such as, for example, in different locations.

In some embodiments, the negative pressure source can be configured to monitor the duration of time the negative pressure source remains in the IPD state 1260. This can be accomplished, for example, by maintaining a timer (in firmware, software, hardware or any combination thereof), which can be reset and started when the negative pressure source transitions into the IPD state 1260. In some embodiments, in order to conserve power, limit the noise and/or vibration generated by the pump, etc., the negative pressure source can be configured to suspend the initial pump down operation for a period of time and, later, retry the initial pump down. This functionality can, for example, conserve battery power and allow transient and/or non-transient leaks to become resolved without user intervention or allow the user to fix the leak (e.g., straighten the dressing, fix the seal, check the connection or connections, etc.).

In some embodiments, when the duration of time for remaining in the IPD state 1260 equals or exceeds a threshold (e.g., 30 seconds), the negative pressure source can be configured to make the transition 1264 to state 1266. In some embodiments, the threshold can be a preset value, such as between 5 seconds or lower and 5 minutes or higher. In some embodiments, the threshold can be set or changed by the user. In some embodiments, the threshold can be varied based on various operating conditions or on any combination thereof. In some embodiments, the negative pressure source can be configured to deactivate the pump when making the transition 1264. The negative pressure source can be configured to monitor a number attempts (e.g., by maintaining a counter which can be reset in state 1252 and updated in wait state 1270) made to establish the first desired negative pressure in the fluid flow path. In some embodiments, the negative pressure source can be configured to provide a limited or maximum number of IPD retry attempts in order, for example, to conserve power. Preferably, the negative pressure source can be configured to provide a limited number of consecutive IPD retry attempts, although the negative pressure source can be configured to provide a limited number of non-consecutive IPD retry attempts or a mix of consecutive and non-consecutive IPD retry attempts. The threshold for IPD retry attempts can be 1, 2, 3, 4, 5, and so on. In some embodiments, the threshold can be a preset value. In some embodiments, the threshold can be set or changed by the user. In some embodiments, the threshold can be varied based on various operating conditions or on any combination thereof.

In some embodiments, the negative pressure source can be configured to determine in state 1266 whether the number of IPD retry attempts made is equal to or exceeds the threshold (e.g., 1 retry attempt). In case the number of IPD retry attempts made is equal or exceeds the threshold, the negative pressure source can be configured to make the transition 1228*a* to the paused state 1218, where therapy is paused or suspended as is described herein. Otherwise, the negative pressure source can be configured to make the transition 1268 to the wait state 1270. In some embodiments, the negative pressure source can be configured to deactivate the source of negative pressure in state 1266, which can provide an indication to the user that the negative pressure source transitioned to state 1266.

In some embodiments, the negative pressure source can be configured to deactivate the pump in the wait state 1270, thereby pausing therapy for a period of time (e.g., between 1 second or less and 1 minute or more, such as 15 seconds). This can be accomplished, for example, by maintaining a timer (in firmware, software, hardware or any combination thereof), which can be reset and started when the negative pressure source transitions into the wait state 1270. This period of time in the wait state 1270 can be preset or variable (e.g., automatically or by the user). In some embodiments, the period of time can be varied based on various operating conditions or on any combination thereof. The period of time the negative pressure source remains in the wait state 1270 can be decreased or increased (e.g., multiplied by a factor between 0.1 or less and 4.0 or more, such as 2), on each transition into the wait state 1270. The period of time can be decreased or increased on each successive transition into the wait state 1270. The period of time can be decreased or increased until it equals or passes a threshold (e.g., between 1 second or less and 5 minutes or more, such as 4 minutes). In addition, the period of time can be reset to an initial value upon transition to a monitor pressure state 1280, transition to the manually paused state 1216, transition to the paused state 1218, etc.

In some embodiments, the negative pressure source can be configured to indicate to the user that the negative pressure source is in the wait state 1270. For example, the negative pressure source can be configured to cause the OK indicator to flash or blink and deactivate the dressing indicator. In some embodiments, deactivating the pump can provide indication that the negative pressure source is in the wait state 1270. Upon expiration of the period of time in the wait state, the negative pressure source can be configured to make the transition 1272 from the wait state 1270 to the IPD state 1260, where the negative pressure source can attempt to establish the first desired negative pressure level in the fluid flow path. In some embodiments, the negative pressure source can be configured to ensure that the negative pressure level under the dressing remains above a certain safety level. For example, the negative pressure source can be configured to maintain the negative pressure level in the fluid flow path above a safety level between −150 mmHg or less and −250 mmHg or more, such as −225 mmHg.

In some embodiments, the retry transitions (e.g., transitions 1264, 1268, and 1272) between the IPD state 1260, state 1266, and the wait state 1270 can detect a leak with high flow, such as a leak that prevents the initial pump down. For example, the retry transitions can detect a leak with a flow of 30 scc/m (e.g., 30 mL/min or any lower or higher suitable flow) or more. A leak having smaller flow may be detected by the transitions (e.g., 1282 and 1284) between states 1280 and 1290 as explained below, but such detection may take a long period of time, such as 30 minutes or more. In certain cases, there is a need to detect a low flow leak quickly. For example, a healthcare professional that may place the dressing on the patient and activate delivery of negative pressure therapy, may need to be quickly alerted that there is a leak so that the healthcare professional can remedy the leak.

In some embodiments, a lower flow leak can be quickly detected by a leak check state 1259, which is entered from the IPD state 1260 (via a transition 1312) prior to initial pump down or directly from the manually paused state 1216 and/or the paused state 1218. In the leak check state 1259, the controller can operate the negative pressure source to provide a lower flow rate in the fluid flow path than, for example, in the IPD state 1260. While the flow rate provided by the negative pressure source may not be sufficient to perform the initial pump down of the wound, the flow rate is nonetheless sufficient to detect if a low flow leak is present in the fluid flow path. For example, the negative pressure source can be configured to provide a flow rate of about 25 scc/m (e.g., 25 mL/min or any other lower or higher suitable flow) in the leak check state 1316. While the negative pressure source operates in such low flow mode, the controller can analyze the change in pressure in the fluid flow path (e.g., under the dressing) to identify signs of successful depressurization, such as whether the pressure in the fluid flow path is decreasing, which is indicative of leak rate (e.g., in dressing seal) being below the negative pressure flow rate and therefore within acceptable levels. On the other hand, if the pressure in the fluid flow path remains static at or below atmospheric pressure, this can be indicative of the leak rate being above the flow rate of the negative pressure source (e.g., 25 scc/m or any other suitable lower or higher flow), which may not be acceptable.

The controller can analyze the change in pressure in the fluid flow path based on multiple pressure readings received from the pressure sensor. For example, a first pressure reading $P_1$ can be taken at time $t_1$ and a second pressure reading $P_2$ can be taken at a subsequent time $t_2$. Times $t_1$ and $t_2$ can be a second or less or more apart. Based on the difference between pressure levels $P_2$ and $P_1$, the controller can determine if the pressure in the fluid flow path is decreasing (e.g., becoming more negative). In some embodiments, more than two pressure readings can be used and multiple pressure readings can be further processed, such as averaged, smoothed, low-pass filtered, etc., to minimize the risk of making an erroneous determination. In some embodiments, change in pressure is analyzed over a period of time, such as 5 seconds or more or less.

In certain implementations, in response to detecting that a leak is present in the fluid flow path, the controller can provide one or more indications to the user. For example, the controller can cause a transition 1316 to the pause state 1218, where therapy is paused or suspended as is described herein. If the controller does not detect presence of a leak, transition 1314 to the IPD state 1260 can be made and the negative pressure source continues to operate as described herein. In some embodiments, detection of a leak in the leak check state 1259 can be performed in a minute or less. In some implementations, detection of a leak can be performed in 10 seconds or less, 30 seconds or less, etc.

In certain embodiments, the leak check state 1259 can be replaced by measuring the rate of pressure change in the fluid flow path when the negative pressure source is deactivated, such as for example in the wait state 1270. However, while the rate of decay of the negative pressure (toward atmospheric pressure) may indicate a presence of a leak, the volume of the wound may need to be known in order to make an accurate determination. In some cases, the volume of the wound is not known a priori. Utilizing the leak check state 1259 as described herein may provide a solution that is independent of the wound volume. Because fluid flow rates are analyzed as described herein, even though a large volume would depressurize more slowly than a small one, the large wound volume would still depressurize due to one or more leaks, which can be detected as described herein.

In some embodiments, a negative pressure source can be calibrated to operate in the leak check state 1259. For example, a drive signal supplied to the actuator of the pump can be selected (e.g., during calibration in manufacturing, etc.) to cause the pump to provide low flow to detect presence of a leak. The drive signal can be selected so that it will not cause the pump to stall. A different drive signal can be used in the IPD state.

In some embodiments, when the first desired negative pressure level in the fluid flow path has been established, the negative pressure source can be configured to make the transition 1276 to a monitor state 1280. The negative pressure source can be configured to reset the number of IPD retry attempts when making the transition 1276. The negative pressure source can be configured to indicate the transition to the monitor state 1280 to the user by, for example, causing the OK indicator to blink or flash and deactivating the dressing indicator. While remaining in the monitor state 1280, the negative pressure source can be configured to deactivate the pump (which can provide an indication to the user that the negative pressure source is in the monitor state 1280) and periodically or continuously monitor the level of pressure in the fluid flow path. The negative pressure source can be configured to measure the level of pressure in the fluid flow path by reading or sampling the sensor.

In some embodiments, the negative pressure source can be configured to determine whether, for example, due to leaks in the system, the level of negative pressure in the fluid flow path decreases to reach and/or pass (e.g., become less than) a threshold. The threshold can be selected from the range between −10 mmHg or less and −100 mmHg or more, such as −60 mmHg. In some embodiments, the threshold can be a preset value, set or changed by the user, and/or varied based on various operating conditions or on any combination thereof. If the threshold is determined to be reached or passed, the negative pressure source can be configured to restore the level of negative pressure in the fluid flow path. In some embodiments, the negative pressure source can be configured to reestablish the first desired negative pressure level or establish another, different negative pressure level. This can be accomplished by making the transition 1282 to a maintenance pump down (MPD) state 1290.

In some embodiments, the negative pressure source can be configured to activate the pump to establish the desired level of negative pressure in the fluid flow path (e.g., the first desired level) while the negative pressure source remains in the MPD state 1290. The negative pressure source can be configured to provide an indication to the user, for example, by causing the OK indicator to blink or flash and deactivating the dressing indicator. In some embodiments, the negative pressure source activating the source of negative pressure can provide an indication to the user that the negative pressure source transitioned to state 1290. In some embodiments, the negative pressure source can be configured to generate less noise and vibration when the pump is activated in the MPD state 1290 than when the pump is activated in the IPD state 1264. For example, the difference in the noise level can be between 1 dB or less and 30 dB or more, such as approximately 7 dB, approximately 20 dB, etc. As another example, the difference in the noise level can be between 30 dB or less to 80 dB or more, such as approximately 45 dB, approximately 50 dB, approximately 65 dB, etc.

In some embodiments, the negative pressure source can be configured to monitor the duration of time it remains in the MPD state 1290. This can be accomplished, for example, by maintaining a timer (in firmware, software, hardware or any combination thereof), which can be reset and started when the negative pressure source makes the transition 1282 into the MPD state 1290. In some embodiments, in order to conserve power, limit the noise and/or vibration generated by the pump, etc., the negative pressure source can be configured to suspend the maintenance pump down operation for a period of time and, later, retry the initial pump down and/or maintenance pump down. This functionality can, for example, conserve battery power and allow transient and/or non-transient leaks to become resolved without user intervention or allow the user to fix the leak (e.g., straighten the dressing, fix the seal, check the connection or connections, etc.).

In some embodiments, when the duration of time in the MPD state 1290 equals or exceeds a threshold (e.g., a value between 5 seconds or lower and 5 minutes or higher, such as 10 seconds) and the pressure level in the fluid flow path has not reached the desired negative pressure level, the negative pressure source can be configured to make the transition 1292 to state 1294. The threshold can be a preset value, set or changed by the user, and/or varied based on various operating conditions or on any combination thereof. In some embodiments, the negative pressure source can be configured to deactivate the pump when making the transition 1292, which can provide an indication to the user that the negative pressure source is making the transition. The negative pressure source can be configured to monitor a number of MPD attempts (e.g., by maintaining a counter which can be reset in the state 1252 and/or when making the transition 1228b and updated when making the transition 1296) made to establish the desired negative pressure in the fluid flow path. In some embodiments, the negative pressure source can be configured to provide a limited or maximum number of MPD retry attempts (e.g., to conserve power). Preferably, the negative pressure source can be configured to provide a limited number of consecutive MPD retry attempts, although the negative pressure source can be configured to provide a limited number of non-consecutive MPD retry attempts or a mix of consecutive and non-consecutive retry attempts. The threshold for MPD retry attempts can be 1, 2, 3, 4, 5, and so on. In some embodiments, the threshold can be a preset value, set or changed by the user, and/or varied based on various operating conditions or on any combination thereof. The negative pressure source can be configured to set the number of IPD and MPD retry attempts to the same or different value. The negative pressure source can be configured to determine in state 1294 whether the number of MPD retry attempts made is equal to or exceeds the threshold (e.g., 3 retry attempts). In case the number of MPD retry attempts made is equal or exceeds the threshold, the negative pressure source can be configured to make the transition 1228b to the paused state 1218, where therapy is paused or suspended as is described herein. Otherwise, the negative pressure source can be configured to make the transition 1296 to the wait state 1270, where therapy is paused or suspended as is described herein. Alternatively, the negative pressure source can be configured to make the transition to the IPD state 1260 or MPD state 1290.

In some embodiments, the negative pressure source can be configured to make the transition 1284 to the monitor state 1280 if the level of pressure under the dressing reaches or exceeds (e.g., become greater than) the desired negative pressure level. The negative pressure source can also be configured to reset the number of MPD retry attempts when making the transition 1284.

In some embodiments, the negative pressure source can be configured to monitor the duty cycle of the source of negative pressure (e.g., pump). The negative pressure source can be configured to monitor the duty cycle periodically and/or continuously. Duty cycle measurements can reflect various operating conditions of the system, such as presence and/or severity of leaks, rate of flow of fluid (e.g., air, liquid and/or solid exudate, etc.) aspirated from wound, and so on. For example, duty cycle measurements can indicate presence of a high leak, and the negative pressure source can be configured to indicate this condition and/or temporarily suspend or pause operation of the pump in order to conserve power. This functionality can, for example, conserve battery power and allow transient and/or non-transient leaks to become resolved without user intervention or allow the user to fix the leak (e.g., straighten the dressing, fix the seal, check the connection or connections, etc.).

In some embodiments, the negative pressure source can be configured to periodically monitor the duty cycle, such as once between every 10 seconds or less and 5 minutes or more. In some embodiments, the negative pressure source can be configured to monitor the duty cycle once per minute. This can be accomplished by maintaining a timer (in firmware, software, hardware or any combination thereof), which can be set to expire every minute (e.g., as is indicated by an interrupt or via polling) and can be restarted (e.g., by clearing an interrupt). In some embodiments, the time interval for measuring the duty cycle can be a preset value, set or changed by the user, and/or varied based on various operating conditions or on any combination thereof. In some embodiments, the negative pressure source can be configured to monitor the duty cycle when the negative pressure source is in the operational state category 1250 (i.e., any of states 1260, 1266, 1270, 1280, 1290, 1294 and/or any transitions between any of the states), as the negative pressure source is configured to activate the pump in this state category. In some embodiments, the negative pressure source can be configured to monitor the duty cycle when the negative pressure source is in a particular state and/or state transition or subset of states and/or state transitions of the operational state category 1250. In some embodiments, the negative pressure source can be configured to monitor the duty cycle when the pump assembly is in a particular state and/or state transition, subset of states and/or state transitions, or all states and/or state transitions of the active state category 1210 or any combination of any states and/or state transitions disclosed herein. As is illustrated in FIG. 3, the negative pressure source can make the transition 1302 from any of states 1260, 1266, 1270, 1280, 1290, 1294 and/or transitions between any of the states to state 1300, where the negative pressure source determines the duty cycle of the pump during the elapsed minute. The duty cycle can be determined according to the equation:

$$DC = t/T, \quad (1)$$

where DC is the duty cycle, t is the duration that the source of negative pressure is active, and T is the total time under consideration. In case of monitoring the duty cycle once per minute (i.e., T=60 seconds), the duty cycle can be expressed (e.g., in percent) as:

$$DC = (\text{Pump run time during the elapsed minute}/60) * 100\% \quad (2)$$

In order to determine the duty cycle, the negative pressure source can be configured to monitor the duration of time that the pump has been active (e.g., the pump run time) and/or inactive.

In some embodiments, the negative pressure source can be configured to compare the determined duty cycle to a duty cycle threshold, which can be selected from the range between 1% or less and 50% or more. The comparison can, for example, indicate presence of a leak in the system. In other words, if the pump is remains active over a period of time so that the duty cycle threshold is reached or exceeded, the pump may be working hard to overcome the leak. In such cases, the negative pressure source can be configured to suspend or pause the delivery of therapy. The negative pressure source can be configured to provide an indication to the user that the pump is working hard (e.g., duty cycle exceeds the duty cycle threshold) by, for example, deactivating the source of negative pressure. In some embodiments, the duty cycle threshold can be a preset value, set or changed by the user, and/or varied based on various operating conditions or on any combination thereof. As is illustrated in FIG. 3, the negative pressure source can be configured to compare the determined duty cycle to the duty cycle threshold (e.g., 9% or another suitable fixed or dynamic threshold). The negative pressure source can be configured to monitor the number of duty cycles that exceed the threshold by, for example, maintaining and updating an overload counter, which can be reset when the negative pressure source transitions from state 1252 to the IPD state 1260.

In some embodiments, the negative pressure source can be configured to update the overload counter in state 1300. If the determined duty cycle does not exceed the duty cycle threshold, the negative pressure source can decrement the overload counter. In some embodiments, the minimum value of overload counter can be set to zero, that is the overload counter cannot become negative. Conversely, if the determined duty cycle is equal to or exceeds the duty cycle threshold, the negative pressure source can increment the overload counter.

In some embodiments, the negative pressure source can be configured to monitor a total or aggregate number of duty cycles that equal to or exceed the duty cycle threshold. This approach can help to smooth or average the duty cycle variation in order to, for example, prevent one or several erratic cycles that may be caused by a transient leak from interrupting therapy. In some embodiments, the negative pressure source can be configured to monitor consecutive or non-consecutive duty cycles exceeding the duty cycle threshold. In some embodiments, the threshold can be a preset value, set or changed by the user, and/or varied based on various operating conditions or on any combination thereof. If the number of duty cycles that exceed the duty cycle threshold is determined to exceed an overload threshold (e.g., a number between 1 and 60 or more, such as 30), the negative pressure source can be configured to make the transition 1230 to the paused state 1216, where therapy is suspended or paused as is described herein. In some embodiments, the negative pressure source can be configured to deactivate the source of negative pressure, which can provide an indication to the user that the pump is working hard (e.g., duty cycle exceeds the overload threshold). If the number of duty cycles that exceed the duty cycle threshold is not determined to exceed the overload threshold, the negative pressure source can be configured to make the transition 1304 and remain in the operational state category 1250. In some embodiments, the negative pressure source can be configured to return to the same state and/or transition between states from which the negative pressure source made the transition 1302. In some embodiments, the negative pressure source can be configured to transition to a different state and/or transition between states.

In some embodiments the negative pressure source is further configured to suspend or pause therapy if the user presses the button 1002 while the negative pressure source is in the operational state category 1250. In some embodiments, the negative pressure source can be configured to transition to the manually paused state 1216.

Figure 4:
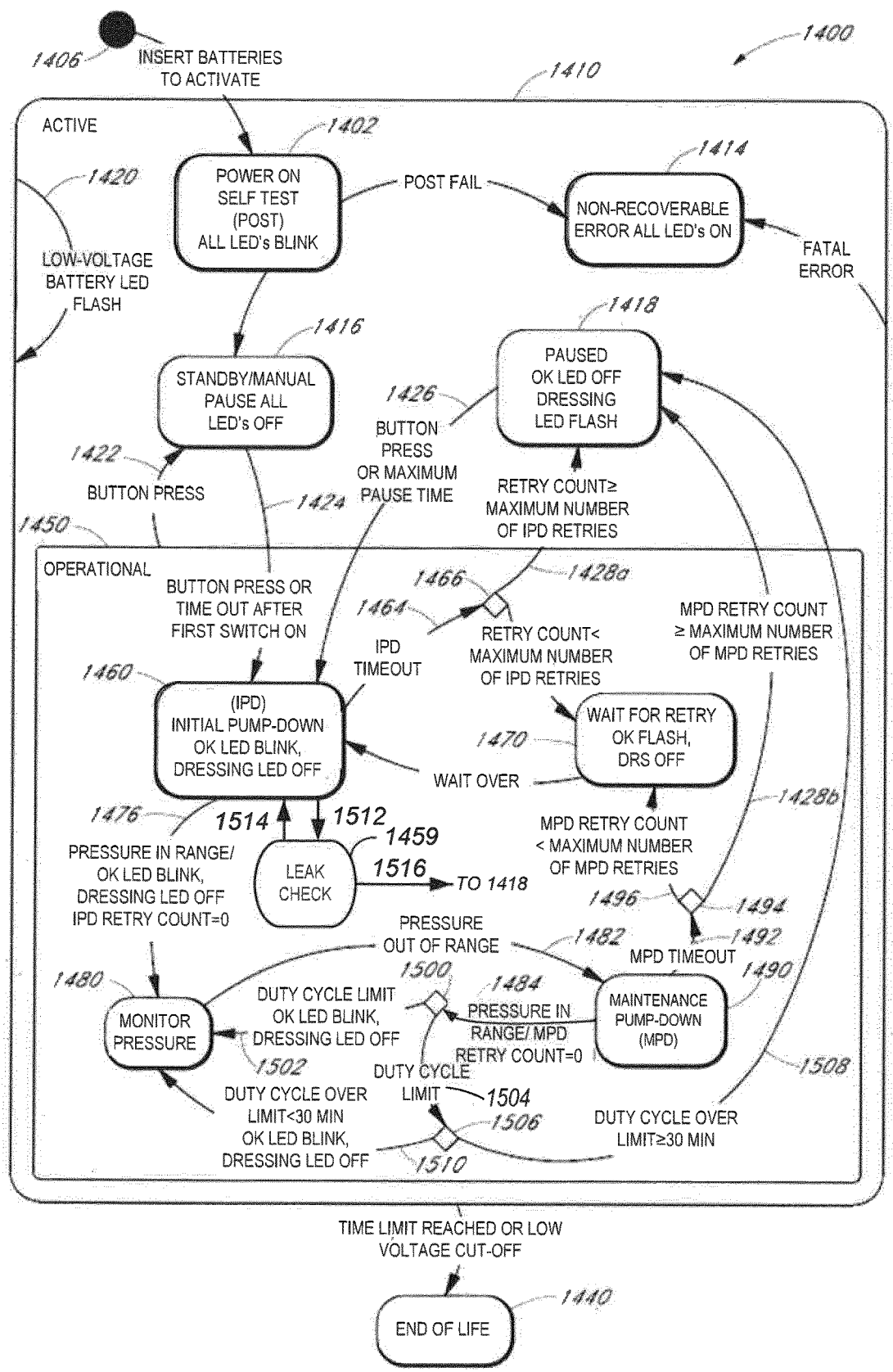
FIG. 4 illustrates another operational state diagram of operation of a negative pressure source according to some embodiments.

FIG. 4 illustrates another state diagram of operation of the negative pressure source 104 according to some embodiments. In some embodiments, the controller can be configured to implement the flow of the state diagram 1400. In some embodiments, the flow 1400 can be largely similar to the flow illustrated in FIGS. 2-3. State 1402 corresponds to state 1202, state 1406 corresponds to state 1260, state category 1410 corresponds to state category 1210, state 1414 corresponds to state 1214, state 1416 corresponds to state 1216, state 1418 corresponds to state 1218, transition 1420 corresponds to transition 1220, transition 1422 corresponds to transition 1222, transition 1424 corresponds to the transition 1224, transition 1426 corresponds to transition 1226, state 1440 corresponds to state 1240, and state 1459 corresponds to the state 1259. In addition, state category 1450 corresponds to state category 1250, state 1460 corresponds to state 1260, transition 1464 corresponds to transition 1264, state 1466 corresponds to transition 1266, transition 1468 corresponds to transition 1268, transition 1428a corresponds to transition 1228a, state 1470 corresponds to state 1270, and transition 1472 corresponds to transition 1272. Further, transition 1476 corresponds to transition 1276, state 1480 corresponds to state 1280, transition 1482 corresponds to transition 1282, state 1490 corresponds to state 1290, transition 1492 corresponds to transition 1292, state 1494 corresponds to state 1294, transition 1496 corresponds to transition 1296, transition 1428b corresponds to transition 1228b, transition 1512 corresponds to transition 1312, transition 1514 corresponds to transition 1314, and transition 1516 corresponds to transition 1316.

In some embodiments, the negative pressure source can be configured to monitor the duty cycle after a desired negative pressure level is established in the fluid flow path in the MPD state 1490. In some embodiments, the negative pressure source can also take into account the duration of time that the pump has been active while the negative pressure source remains in the IPD state 1460. As is illustrated, the device can be configured to make the transition 1484 from the MPD state 1490. Transition 1484 can be similar to the transition 1284, but instead of transitioning directly to the IPD state 1480, the negative pressure source can be configured to monitor the duty cycle in state 1500. In some embodiments, the negative pressure source can be configured to monitor the duty cycle during a cumulative period of time that the negative pressure source has remained in the monitor state 1480 and MPD state 1490. In some embodiments, the negative pressure source can be configured to monitor the duty cycle over the cumulative period of time during the immediately preceding or previous monitor and MPD cycles. For example, immediately before transitioning to state 1500 the negative pressure source could have remained in the MPD state 1490 for time duration X (during which the pump was active). In addition, assuming that immediately before transitioning to the MPD state 1490, the negative pressure source remained in the monitor state 1480 for a time duration Y (during which the pump was not active), the duty cycle (DC) can be expressed (e.g., in percent) as:

$$DC=100\%*[X/(X+Y)]. \quad (3)$$

In order to determine the duty cycle, the negative pressure source can be configured to monitor the duration of time that the pump has been active and/or inactive.

In some embodiments, the negative pressure source can be configured to compare the determined duty cycle to a duty cycle threshold, as is described herein. In some embodiments, the threshold can be a preset value, set or changed by the user, and/or varied based on various operating conditions or on any combination thereof. If the duty cycle is determined to be below the threshold, the negative pressure source can be configured to make the transition 1502 to the monitor state 1480. Conversely, if the duty cycle is determined to be equal to or exceed the threshold, the negative pressure source can be configured to make the transition 1504 to state 1506. In some embodiments, the negative pressure source can provide an indication that the duty cycle exceeds the threshold by, for example, deactivating the pump.

In some embodiments, the negative pressure source can be configured to monitor a total or aggregate time over which the duty cycle is equal to or exceeds the threshold. This approach can help to smooth or average the duty cycle variation in order to, for example, prevent one or several erratic cycles that may be caused by a transient leak from interrupting therapy. Monitoring can be accomplished by maintaining a timer (in firmware, software, hardware or any combination thereof), which can be restarted (e.g., on the transition 1476) and updated (e.g., in state 1506). In some embodiments, the negative pressure source can be configured to determine whether the duty cycle equals to or exceeds the threshold over a certain aggregate period of time, which can be compared to an aggregate duration threshold. The threshold can be selected from a range between 5 minutes or less and 2 hours or more, such as 30 minutes. In some embodiments, the threshold can be a preset value, set or changed by the user, and/or varied based on various operating conditions or on any combination thereof. If the aggregate period of time equals to or exceeds the threshold, the negative pressure source can be configured to make the transition 1508 to the paused state 1418, where the negative pressure source can be configured to suspend or pause the delivery of therapy. In some embodiments, the negative pressure source can indicate this transition to the user by, for example, deactivating the pump. Conversely, if the aggregate period of time is determined to be less than the threshold, the negative pressure source can be configured to make the transition 1510 to the monitor state 1480. The pump assembly can be configured to indicate the transition 1510 to the user by, for example, causing the OK indicator to blink or flash and deactivating the dressing indicator.

Other Variations

Additional embodiments of controlling the negative pressure source as described in U.S. Pat. No. 8,905,985, the entirety of which is incorporated herein by reference. Additional embodiments of calibrating the drive signal of a pump are described in PCT Publication No. WO 2016103035, the entirety of which is incorporated herein by reference. The embodiments described herein are compatible with and can be part of the embodiments described in these publications, and some or all of the features described herein can be used or otherwise combined with any of the features described in these publications.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method of operating a negative pressure wound therapy apparatus, the method comprising:
by a controller of the negative pressure wound therapy apparatus, in response to a request for initiating or restarting application of negative pressure:
prior to initiating a negative pressure source of the negative pressure wound therapy apparatus to reduce pressure in a fluid flow path from atmospheric pressure to a negative pressure set point, operating the negative pressure source to provide a first level of negative pressure via the fluid flow path to a wound covered by a wound dressing;
determining a change in pressure in the fluid flow path over a first period of time;
in response to determining that pressure in the fluid flow path is decreasing relative to atmospheric pressure, operating the negative pressure source to provide a second level of negative pressure that is greater than the first level of negative pressure; and
in response to determining that pressure in the fluid flow path is not decreasing relative to atmospheric pressure, providing an indication of a first leak in a seal formed by the wound dressing.

2. The method of claim 1, wherein:
the request for initiating or restarting application of negative pressure is associated with the negative pressure set point to be established in the fluid flow path;
the first level of negative pressure is insufficient to reduce pressure in the fluid flow path to establish the negative pressure set point; and
the second level of negative pressure is sufficient to reduce pressure in fluid flow path to establish the negative pressure set point.

3. The method of claim 2, further comprising, in response to a determining that the negative pressure set point has been established:
deactivating the negative pressure source; and
subsequent to the deactivating, alternating activation and deactivation of the negative pressure source to reestablish the negative pressure set point in the fluid flow path.

4. The method of claim 2, wherein initiating the negative pressure source to reduce pressure in the fluid flow path from atmospheric pressure to the negative pressure set point comprises:
activating the negative pressure source to reduce pressure in the fluid flow path to the negative pressure set point;
in response to determining that pressure in the fluid flow path has not reached the negative pressure set point during a second period of time, deactivating the negative pressure source for a third period of time; and
in response to determining that the third period of time has elapsed, activating the negative pressure source to reduce pressure in the fluid flow path to establish the negative pressure set point.

5. The method of claim 4, wherein establishing the negative pressure set point comprises alternately activating and deactivating the negative pressure source.

6. The method of claim 5, further comprising monitoring a duty cycle of the negative pressure source and providing an indication of a second leak in the seal in response to determining that the duty cycle satisfies a duty cycle threshold.

7. The method of claim 6, wherein the first leak comprises a leak of smaller intensity than the second leak.

8. The method of claim 6, wherein the indication of at least one of the first or second leaks in the seal comprises deactivating the negative pressure source.

9. The method of claim 5, further comprising monitoring a number of deactivations of the negative pressure source over the third period of time.

10. The method of claim 9, further comprising providing an indication of a second leak in the seal in response to determining that the number of deactivations of the negative pressure source satisfies a retry threshold.

11. The method of claim 10, wherein the first leak comprises a leak of smaller intensity than the second leak.

12. The method of claim 10, wherein the indication of at least one of the first or second leaks in the seal comprises deactivating the negative pressure source.

13. The method of claim 1, wherein operating the negative pressure source to provide the first level of negative pressure comprises establishing a flow rate of 25 mL/min in the fluid flow path.

14. The method of claim 13, wherein the indication of the first leak in the seal corresponds to an indication of a leak with a flow rate of 25 mL/min or more.

15. The method of claim 1, wherein determining the change in pressure in the fluid flow path is further based on determining a difference in a first pressure in the fluid flow path measured at a first time and a second pressure in the fluid flow path measured at a second time subsequent to the first time.

16. The method of claim 1, wherein operating the negative pressure source prior to initiating the negative pressure source to reduce pressure in the fluid flow path from atmospheric pressure to the negative pressure set point comprises operating the negative pressure source in a low flow mode.

17. The method of any of claim 1, wherein operating the negative pressure source prior to initiating the negative pressure source to reduce pressure in the fluid flow path from atmospheric pressure to the negative pressure set point comprises providing a first drive signal to an actuator of the negative pressure source.

18. The method of claim 17, wherein initiating the negative pressure source to reduce pressure in the fluid flow path from atmospheric pressure to the negative pressure set point comprises providing a second drive signal to the actuator of the negative pressure source, the second drive signal being different from the first drive signal.

19. The method of claim 1, wherein the request for initiating or restarting application of negative pressure comprises activation of a switch, and wherein switch is the only switch positioned on an external surface of a housing of the negative pressure wound therapy apparatus.

20. The method of claim 1, wherein the negative pressure wound therapy apparatus does not include a canister configured to store fluid aspirated from the wound.

* * * * *

UNITED STATES PATENT AND TRADEMARK OFFICE
CERTIFICATE OF CORRECTION

PATENT NO. : 11,564,846 B2
APPLICATION NO. : 17/505356
DATED : January 31, 2023
INVENTOR(S) : Ben Alan Askem It is certified that error appears in the above-identified patent and that said Letters Patent is hereby corrected as shown below:

On the Title Page

Column 2 Item (56) (Other Publications), Line 1, delete "Reporton" and insert -- Report on --.

In the Drawings

Sheet 3 of 4, (Reference Numeral 1280) (FIG. 3), Line 3, delete "DRESSNG" and insert -- DRESSING --.

Sheet 3 of 4, (FIG. 3), Line 26 (approx.), delete "UDPATED" and insert -- UPDATED --.

In the Specification

Column 1, Line 11, delete "No," and insert -- No. --.

Column 12, Line 53, after "number" insert -- of --.

Column 13, Line 66, delete "scc/m" and insert -- sccm --.

Column 14, Line 23, delete "scc/m" and insert -- sccm --.

Column 14, Line 35, delete "scc/m" and insert -- sccm --.

In the Claims

Column 24, Line 42, Claim 17, delete "of any of" and insert -- of --.

Signed and Sealed this
Ninth Day of May, 2023

Katherine Kelly Vidal
*Director of the United States Patent and Trademark Office*